US012773278B2

(12) United States Patent
Stroosma et al.

(10) Patent No.: US 12,773,278 B2
(45) Date of Patent: Oct. 27, 2026

(54) IMAGE GUIDED INTERVENTION METHOD AND SYSTEM

(71) Applicant: KONINKLIJKE PHILIPS N.V., Eindhoven (NL)

(72) Inventors: Otto Bernardus Stroosma, Eindhoven (NL); Guillaume Leopold Theodorus Frederik Hautvast, Veldhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 19/113,046

(22) PCT Filed: Sep. 6, 2023

(86) PCT No.: PCT/EP2023/074353
§ 371 (c)(1),
(2) Date: Mar. 19, 2025

(87) PCT Pub. No.: WO2024/061621
PCT Pub. Date: Mar. 28, 2024

(65) Prior Publication Data
US 2026/0096856 A1 Apr. 9, 2026

(30) Foreign Application Priority Data
Sep. 20, 2022 (EP) .................................... 22196542

(51) Int. Cl.
*A61B 34/20* (2016.01)
*A61B 6/00* (2024.01)
(Continued)

(52) U.S. Cl.
CPC .............. *A61B 34/20* (2016.02); *A61B 6/032* (2013.01); *A61B 6/12* (2013.01); *A61B 6/4085* (2013.01);
(Continued)

(58) Field of Classification Search
CPC ........... A61B 6/12; A61B 34/20; A61B 6/032; A61B 6/4085; A61B 6/4405; A61B 6/463; A61B 6/566
See application file for complete search history.

(56) References Cited

U.S. PATENT DOCUMENTS

| | | | | |
|---|---|---|---|---|
| 2014/0073907 | A1 * | 3/2014 | Kumar | A61B 10/0241 600/407 |
| 2020/0352543 | A1 * | 11/2020 | DeFreitas | A61B 8/466 |
| 2022/0000565 | A1 * | 1/2022 | Gururaj | A61B 17/34 |

FOREIGN PATENT DOCUMENTS

| | | | |
|---|---|---|---|
| CN | 110025379 | A | 7/2019 |
| DE | 102020211547 | A1 | 3/2022 |

OTHER PUBLICATIONS

Kingma et al.; Intraoperative cone beam computed tomography for detecting residual stones in percutaneous nephrolithotomy: a feasibility study; Urolithiasis 49, 551-557 (2021). Published Mar. 8, 2021 (Year: 2021).*

(Continued)

*Primary Examiner* — Chao Sheng

(57) ABSTRACT

A method and system for guiding renal stone removal. The method includes steps for facilitating or guiding three stages of the intervention: renal access, stone removal, and a stone-free check. This is facilitated by a method which includes three stages: an intra-operative image guidance phase for obtaining CT-based imagery of the renal area; a renal access guidance phase in which the aforementioned CT-based imagery is used to generate intervention guidance imagery to guide renal access, and a stone-free check phase in which further intra-operative CT images are acquired to check the stone-free status of the patient.

20 Claims, 2 Drawing Sheets

(51) Int. Cl.
*A61B 6/03* (2006.01)
*A61B 6/12* (2006.01)
*A61B 6/40* (2024.01)
*A61B 6/46* (2024.01)

(52) U.S. Cl.
CPC ............ *A61B 6/4405* (2013.01); *A61B 6/463* (2013.01); *A61B 6/566* (2013.01)

(56) References Cited

OTHER PUBLICATIONS

Hawkins et al., "Use of cone-beam CT and live 3-D needle guidance to facilitate percutaneous nephrostomy and nephrolithotripsy access in children and adolescents", Pediatric Radiology, vol. 46 Issue 4, pp. 570-574, (2016).
Busser et al., "Cone beam CT guidance provides superior accuracy for complex needle paths compared with CT guidance", British Journal of Radiology, vol. 86 Issue 1030, p. 20130310, (2013).
Jiao et al., "Flat detector cone beam CT-guided nephrostomy using virtual navigation in patients with iatrogenic ureteral injury", La radiologia medica, vol. 122 Issue 8, pp. 557-563, (2017).
Nguyen et al., "Percutaneous Nephrolithotomy Access: A Systematic Review of Intraoperative Assistive Technologies", Journal of Endourology, vol. 33 Issue 5, pp. 358-368, (2019).
Tomaszweski et al., "Renal access by urologist or radiologist during percutaneous nephrolithotomy", Journal of Endourology 24:, pp. 1733-1737, (2010).
Olvera-Posada et al., "Natural History of Residual Fragments After Percutaneous Nephrolithotomy: Evaluation of Factors Related to Clinical Events and Intervention", Urology 97, pp. 46-50, (2016).
Raman et al., "Natural history of residual fragments following percutaneous nephrostolithotomy", Journal of Urology, vol. 181, Issue 3, pp. 1163-1168, (2009).
Kingma et al., "Intraoperative cone beam computed tomography for detecting residual stones in percutaneous nephrolithotomy: a feasibility study" Urolithiasis, vol. 49 Issue 6, pp. 551-557, (2021).
Rassweiler-Seyfried et al., "Navigierter perkutaner Zugang zur Niere", Der Urologe, Springer Medizin, Heidelberg, vol. 59, No. 9, Jun. 12, 2020, pp. 1017-1025.
International Search report and Written Opinion of PCT/EP2023/074353, dated Oct. 9, 2023.

* cited by examiner

IMAGE GUIDED INTERVENTION METHOD AND SYSTEM

CROSS-REFERENCE TO PRIOR APPLICATIONS

This application is the U.S. National Phase application under 35 U.S.C. § 371 of International Application No. PCT/EP2023/074353, filed on Sep. 6, 2023, which claims the benefit of European Patent Application No. 22196542.9, filed on Sep. 20, 2022. These applications are hereby incorporated by reference herein.

FIELD OF THE INVENTION

This invention relates to the field of image-guided intervention, particularly in the field urology, for example in the field of renal intervention, for example for kidney stone removal.

BACKGROUND OF THE INVENTION

Within the field of image-guided interventions, there remain challenges in balancing the efficiency of the interventional workflow with patient safety, and with surgical success rate.

One area of particular interest which has motivated the making of the present invention is image guided intervention in the field of urology, and more specifically of image guidance during percutaneous nephrolithotripsy (PCNL).

In urolithiasis, or kidney stone disease, stones in the urinary collecting system develop which can cause blockage of the ureter resulting in severe pain in the lower back or abdomen. The lifetime prevalence of urolithiasis is approximately 12% for men and 7% for women in the United States, and it is rising, possibly due to dietary factors.

Urolithiasis can be treated by disintegration and/or removal of the stones using either extracorporeal shockwave lithotripsy (ESWL), ureterorenoscopy (URS), or PCNL. Treatments are selected based on the location, size and hardness of the stone, with PCNL being the option of choice for larger (>2 cm in diameter) stones.

PCNL procedures are typically performed by a team of medical specialists consisting of a urologist, a sterile nurse, a non-sterile nurse, often an interventional radiologist, a radiology technician, an anesthesiologist, an anesthesiology assistant, and possibly others.

While there are many workflow variations in performing PCNL procedures, a typical procedure involves a collaboration between the interventional radiologist and the urologist. The interventional radiologist starts by gaining renal access using fluoroscopic and/or ultrasound image guidance, while the patient is under local anesthesia. If necessary, this includes contrast administration through the inserted needle to improve fluoroscopic imaging.

Once renal access is confirmed by urine flow through the needle, a guidewire is inserted and the patient will be transported from the interventional radiology suite to the operating room, where the patient will receive general anesthesia and be placed in either prone or supine position. The urologist will then use the guidewire to dilate the access up to a 1 cm diameter, insert an endoscope into the urinary collecting system of the kidney and subsequently perform the lithotripsy. Larger stone fragments may be collected through the access sheath, while smaller ones flush out automatically.

Fluoroscopy and nephroscope imaging will be used to verify if all stone fragments are removed. Ultimately, renal drainage needs to be secured by placing either a JJ catheter or nephrostomy tube under fluoroscopy guidance, and the access sheath can be removed, closing the incision with a suture.

After the procedure, the stone free status of the patient needs to be confirmed with a diagnostic CT exam that is usually performed one week after the procedure.

Clinical outcome of PCNL procedures are highly dependent on the renal access strategy. In order to successfully remove a stone, it is important to gain access through the correct calyx, such that the urologist can easily reach the stone and visualize residual fragments if present.

The removal of kidney stones using PCNL is a challenging clinical procedure, the success of which is highly dependent on the renal access. The optimal access strategy to reach the stone needs to be determined and—to avoid complications—the calyx needs to be approached at the correct angle. Urologists often need to be supported by interventional radiologists to obtain renal access. In current clinical practice, obtaining renal access requires complex 3D navigation skills based on either 2D projective, real-time fluoroscopic or a combination of fluoroscopic and ultrasound imaging. Errors in this process may lead to unusable access, or not obtaining access at all. Renal access gained through the wrong calyx is associated with a decreased stone free rate. Inadequate renal access is associated with complications such as injury of branches of the renal artery causing (severe) bleeding, colon perforation or lung injury causing pneumothorax. In this regard, reference is made for example to the paper: J. J. Tomaszweski et al., Renal access by urologist or radiologist during percutaneous nephrolithotomy. Journal of Endourology 24:1733-1737, 2010.

After gaining renal access, the urologist will begin disintegrating kidney stones, which may result in residual stone fragments becoming lodged in the calyces of the kidney or the proximal ureter. To identify these during the procedure, the urologist will use per-operative (intra-operative) fluoroscopic and endoscopic imaging. As noted above, this process also is verified sometime after the procedure, e.g. 1 week, by post-operative CT imaging to confirm the stone free status of the patient. In fact, the post-operative check reveals residual stone fragments in up to 25% of cases. Up to 73% of these patients need to undergo additional treatments such as ESWL, URS or PCNL. In this regard reference is made to the papers:

D. Olvera-Posada et al., Natural History of Residual Fragments After Percutaneous Nephrolithotomy: Evaluation of Factors Related to Clinical Events and Intervention, Urology 97:46-50, 2016; and J. D. Raman et al., Natural history of residual fragments following percutaneous nephrostolithotomy, Journal of Urology, 181(3):1163-1168, 2009.

The complexities of gaining renal access and confirming stone free status not only impact negatively on patient outcomes, but also make urologists dependent upon other medical specialists such as the interventional and diagnostic radiologists. This is associated with various clinical workflow difficulties and substantial impact on the cost of these procedures.

Improvements in this area would generally be of benefit.

SUMMARY OF THE INVENTION

The invention is defined by the claims. Dependent claims define advantageous embodiments.

According to examples in accordance with an aspect of the invention, there is provided a processing unit comprising one or more processors configured to perform a computer-implemented method for interventional support during a renal interventional procedure for kidney stone removal.

The method comprises at least one intra-operative image acquisition phase, which comprises: receiving computed tomography (CT) image data of an anatomical area which includes at least a portion of a kidney of a subject.

The method further comprises an interventional image guidance phase, comprising: receiving real-time tool tracking data indicative of a positioning of an interventional tool for use in the interventional procedure; generating real-time guidance imagery based on the CT image data, and further based on the tracking data, the guidance imagery visualizing a position of the interventional tool relative to the anatomical area imaged in the received CT image data; and communicating with a user interface device to display the generated guidance imagery in real time on a display unit of the user-interface device.

The method further comprises a quality assurance check phase, following the interventional image guidance phase, comprising: communicating with a CT imaging apparatus to acquire further CT image data of said anatomical area using a CT imaging apparatus, for use in visualizing any residual stones or stone fragments, for example for determining whether complete stone removal has been achieved. The further CT image data is preferably cone beam CT image data. The CT imaging apparatus used to acquire the further CT image data may be a C-arm CT apparatus or flat-panel CT-apparatus. It may be a cone-beam CT apparatus. The further CT image data may be cone-beam CT image data.

The method further comprises communicating with the user-interface device to display the further CT image data on the display unit of the user interface.

The proposed method advantageously facilitates performance of all stages of a stone removal procedure in one operation and by one leading surgeon, namely: renal access, stone removal, and stone-free check. This is facilitated by CT image-based interventional guidance which guides the surgeon in gaining renal access, in combination with use of intra-operative CT imagery to check the stone free status before renal access is removed.

A motivating aim of the inventors in making this invention is to reduce the complexity of gaining renal access, particularly in PCNL procedures, and improving stone free success rate of the procedure. By performing the stone free check contemporaneously with the procedure, before renal access has been closed, this improves the likelihood of stone-free status, since any residual stone fragments can be addressed immediately by further intervention steps.

In some embodiments, the method further comprises obtaining an indication of a result of the quality assurance check phase, and responsive to the result of the quality assurance check indicating incomplete stone removal, controlling execution of a further iteration of the interventional image-guidance phase, and subsequently a further execution of the quality assurance check phase. A further iteration of the interventional image-guidance phase means controlling generation of further guidance imagery for example.

A result of the quality assurance check phase can be obtained either manually from a user, or automatically based on image analysis. For example, in some embodiments, the indication of the result of the quality assurance check is obtained based on a user input received at the user interface device. In some embodiments, the indication of the result of the quality assurance check is obtained based on application of a stone removal check algorithm to the obtained further CT image data to automatically determine complete or incomplete stone removal.

In some embodiments, the quality assurance check phase comprises: obtaining, based on user input or based on application of an automated segmentation algorithm, location information associated with any residual stones present in the kidney. In some embodiments, during the aforementioned further iteration of the image guidance phase, the guidance imagery may include a visualization of the location information associated with residual stones.

In some embodiments the quality assurance check phase is triggered responsive to receipt of a pre-defined user input command from the user interface.

In some embodiments, the at least one intra-operative image acquisition phase comprises communicating with a CT imaging apparatus to acquire CT image data of said anatomical area using a CT imaging apparatus. Preferably a cone beam CT image data is acquired. The CT imaging apparatus may be a cone beam CT imaging apparatus. It may be a C-arm CT imaging apparatus or flat-panel CT imaging apparatus.

In some embodiments, the guidance imagery comprises a visual overlay indicative of a position of the interventional tool fused with an anatomical image representative of the anatomical area, the anatomical image being based on the CT image data acquired in the intra-operative image acquisition phase. The anatomical image could be the CT image alone, or could be a synthetic fused image formed from the CT image and a pre-operative image for example.

In some embodiments, the guidance imagery includes one or more visual overlays providing navigation guidance for navigating insertion of the interventional tool along a pre-defined tool entry path from an incision point on the skin to a pre-defined entry point of the kidney.

In some embodiments, the aforementioned one or more visual overlays providing navigation guidance provide a visual indication of a target location of the incision point (e.g. relative to the patient anatomy) and an indication of a target angle of insertion for the tool.

In some advantageous embodiments, the method may comprise an intervention planning phase. The intervention planning phase may comprise obtaining an indication of a planned entry point of the kidney. The intervention planning phase may further comprise obtaining an indication of a planned entry path through the body to the entry point of the kidney. In some embodiments, the one or more visual overlays for providing navigation guidance may be generated based on said obtained indications.

In some embodiments, the indication of the planned entry point of the kidney may comprises an indication of a planned Calyx of the kidney through which kidney entry is to be achieved.

In some embodiments, the method may comprise obtaining an indication of a planned calyx for entry to the kidney, manually or automatically segmenting the said planned calyx within the received CT image data, and identifying a location of a planned entry point of the kidney relative to the CT image data based thereon.

In some embodiments, the aforementioned indication of the planned calyx of the kidney through which kidney entry is to be achieved may be obtained based on a user input received at the user interface. In some embodiments, the aforementioned planned entry path through the body and the planned incision point are determined automatically, for example based on the indication of the planned calyx of the kidney through which kidney entry is to be achieved.

With regards to the guidance imagery, in some embodiments, this may be generated by generating synthetic image data by fusing the CT image data received during the at least one intra-operative image acquisition phase with pre-operative image data of the same anatomical area of the same patient retrieved from a datastore. The benefit of this is that the pre-operative image data might be obtained with higher resolution than is possible or practical to obtain intra-operatively (i.e. contemporaneously with the intervention procedure), and thus detail can be enhanced. Also, pre-operative imagery could be obtained with a same or different modality, allowing potentially additional detail to be added by the fusion. Furthermore, even where the same modality is used, the pre-operative image might be further enhanced for example by contrast enhancement in some cases.

For example, in some embodiments, the CT image data acquired in the at least one intra-operative image acquisition phase is non-contrast-enhanced cone beam CT image data, and wherein the method comprises generating a synthetic image by fusing the acquired non-contrast enhanced CT image data with pre-operative contrast enhanced cone-beam CT image data of the same anatomical area of the same patient retrieved from a datastore.

However, it is also a possibility that in other embodiments, the CT image data acquired in the at least one intra-operative image acquisition phase is contrast-enhanced cone beam CT image data.

In some embodiments, not only the intraoperative CT imagery is used to assist intervention, but also other modalities of imaging. For example, the image guidance phase may further comprise receiving supplementary image data comprising one or more of: real-time endoscopic imaging data from an endoscopic imaging system; real-time ultrasound imaging data from an ultrasound imaging system; real-time fluoroscopic imaging data from a cone-beam CT imaging apparatus. These modalities complement and enhance the CT image data since they enable real-time imaging, whereas real-time CT imaging (at a sufficient temporal resolution to be used for interventional guidance) is simply not (with the present state of the art) a practical possibility. The radiation dose resulting from this would also be prohibitive.

In some embodiments, the image guidance phase comprises communicating with the user interface to simultaneously display the guidance imagery and the supplementary image data. This thereby creates a multi-modality display output on the display unit.

In some embodiments, the processing unit further comprises a communication interface for wired or wireless connection to one or more of: a cone-beam CT imaging apparatus; a user interface device, a tool tracking system, and an ultrasound imaging system and/or an endoscopic imaging system.

The invention could be embodied in the form of an ambulatory base station being moveable within an operating room, and comprising a processing unit in accordance with any of the embodiments described in this document, or in accordance with any claim. This therefore provides a mobile cart which can act as a hub for connection of all hardware, and which houses the processing unit which facilitates the computer-implemented method. For example, the ambulatory unit comprises a base station mounted on rollers or wheels. This has the advantage of enabling the system to be wheeled between different operating rooms, avoiding the need to fully re-fit an operating room with permanently installed equipment to perform the procedure. Existing operating rooms could immediately be used to perform the method. The ambulatory base station might indeed further include the aforementioned user interface with display unit, to avoid a need to manually connect and set-up a video output from the processing unit to existing display equipment in the operating room.

Another aspect of the invention is a system, comprising: a processing unit according to any of the embodiments or examples described in this disclosure, or an ambulatory base station comprising such a processing unit; an intra-operative cone-beam CT imaging apparatus; and a tracking system for tracking a positioning of an interventional tool within the body of a patient. The intra-operative cone-beam CT imaging apparatus may be moveable in and out of an imaging position relative to the patient, without moving the patient. For example, it might have a C-arm construction.

Another aspect of the invention is a computer-implemented method for interventional support during a renal interventional procedure for kidney stone removal. The method comprises at least one intra-operative image acquisition phase, which comprises: receiving computed tomography (CT) image data of an anatomical area which includes at least a portion of a kidney of a subject.

The method further comprises an interventional image guidance phase, comprising: receiving real-time tool tracking data indicative of a positioning of an interventional tool for use in the interventional procedure; generating real-time guidance imagery based on the CT image data, and further based on the tracking data, the guidance imagery visualizing a position of the interventional tool relative to the anatomical area imaged in the received CT image data; and communicating with a user interface device to display the generated guidance imagery in real time on a display unit of the user-interface device.

In some embodiments receiving real-time tool tracking can be based on image-guidance methods and can include post- or pre-operative imagery and not just real-time methods. In other words, the application can be broadened to different kinds of imaging equipment (e.g. MR, US, PET, SPECT) and not only based on CT or cone beam CT.

The method further comprises a quality assurance check phase, following the interventional image guidance phase, comprising: communicating with a CT imaging apparatus to acquire further CT image data of said anatomical area using a CT imaging apparatus, for use in visualizing any residual stones or stone fragments, for example for use thereby in determining whether complete stone removal has been achieved. The further CT image data is preferably cone beam CT image data.

The method further comprises communicating with the user-interface device to display the further CT image data on the display unit of the user interface.

Another aspect of the invention is a computer program product comprising computer program code configured, when run on a processor, to cause the processor to perform a method in accordance with any embodiment described in this document, or in accordance with any claim.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
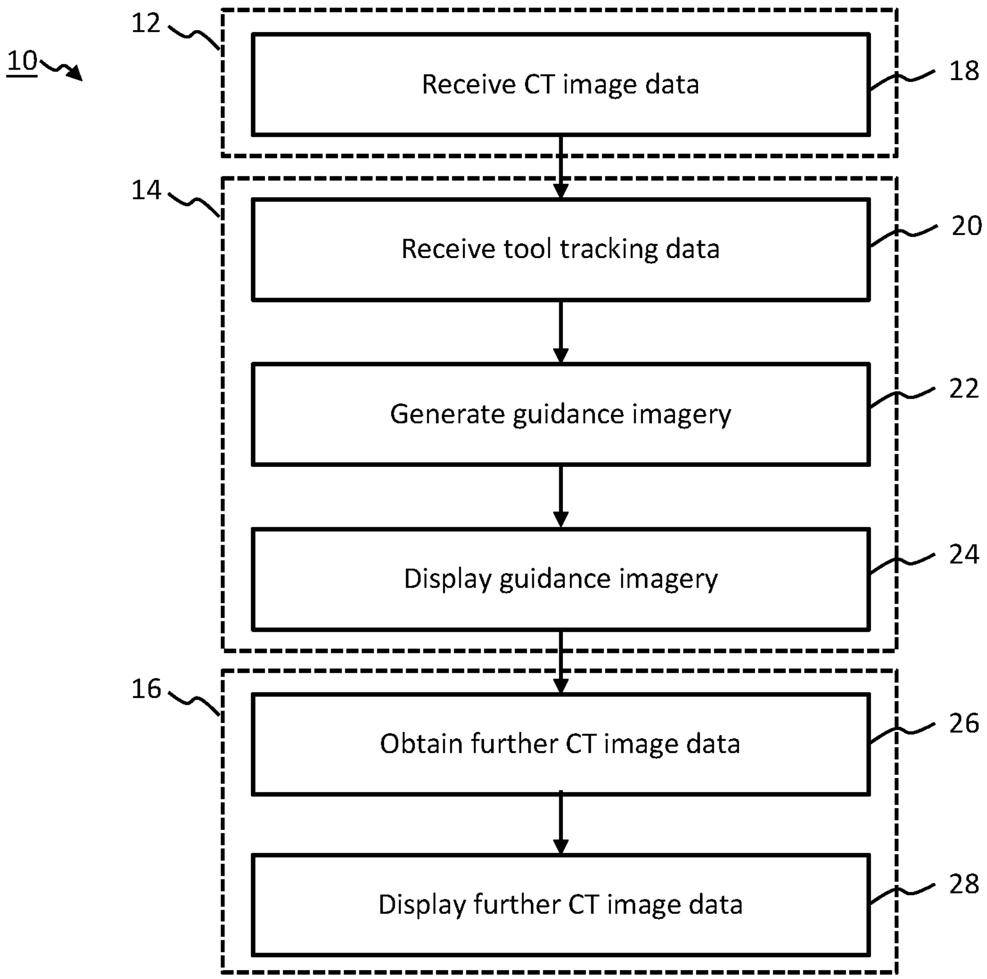
FIG. 1 outlines steps of an example method in accordance with one or more embodiments of the invention.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a method and system for guiding renal stone removal in a single procedure, wherein for example all steps can be performed by one leading surgeon, and furthermore a method which improves the resulting stone-free rate of the procedure. In particular, the method includes steps for facilitating or guiding three stages of the intervention: renal access, stone removal, and a stone-free check. This is facilitated by a method which includes three stages: an intra-operative image guidance phase for obtaining CT-based imagery of the renal area; a renal access guidance phase in which the aforementioned CT-based imagery is used to generate intervention guidance imagery to guide renal access along an access path, and a stone-free check phase in which further intra-operative CT images are acquired to check the stone-free status of the patient. Cone beam CT (CBCT) imagery is preferably used for the last stage, since this is associated with a lower radiation dose to the patient for the same spatial resolution of imagery. It also preferred because it can be more readily available in an operating room compared to conventional cone-beam CT imaging, e.g. helical or axial fan-beam imaging. It is also preferred because it permits acquisition using a smaller and simpler apparatus structure. For example, a C-arm or flat-panel CT apparatus can be used in cone-beam imagery, making access to the patient easier compared to a system with a circularly rotating gantry.

A motivating aim of the inventors in making this invention has been to reduce the complexity of gaining renal access, particularly in PCNL procedures, and improving stone free success rate of the procedure. By performing the stone free check contemporaneously with the procedure, before renal access has been closed, this improves the likelihood of stone-free status, since any residual stone fragments can be addressed immediately by further intervention steps.

The above aim is achieved with a system and method for needle guidance with tool tracking and CBCT imaging.

To explain further, typically a PCNL procedure involves two separately performed stages: a renal access stage, and a stone removal stage. These are typically performed by separate clinicians. In the US, in 90% of cases, renal access for PCNL procedures is gained by an interventional radiologist. The interventional radiologist starts by gaining renal access using fluoroscopic or ultrasound image guidance, while the patient is under local anesthesia. A guidewire is inserted once access is gained. At this point, the patient will be transported from the interventional radiology suite to the operating room, where the patient will receive general anesthesia. The stone removal procedure then begins.

This division in the interventional workflow creates additional overhead and procedure inefficiencies. An aim of embodiments of the present invention is to simplify the workflow, which results in procedure simplification, decreased communication mistakes with regards to the access strategy, cost reduction for the hospital and improved patient satisfaction. A system and method for therapy guidance is proposed. In particular a system is proposed which can perform at least both of the following operations: a renal access guidance operation for guiding needle navigation based on per-operative (intra-operative) CT images (preferably cone beam CT images); and a stone free check operation enabling confirmation of stone free status based on per-operative (intra-operative) CT images (preferably cone beam CT images).

As will be discussed further, it is envisaged that the therapy guidance and evaluation method according to at least one set of embodiments may be embodied or implemented by a hardware system that comprises: a cone beam computed tomography (CBCT) image acquisition apparatus; an interventional tool tracking unit; a computing unit (to host dedicated application software which is configured to execute the steps of the computer-implemented method); and a display.

FIG. 1 outlines in block diagram form steps of an example computer implemented method 10 according to one or more embodiments. The steps will be recited in summary, before being explained further in the form of example embodiments. The method 10 is, for example, for providing interventional support during a renal interventional procedure, for kidney stone removal.

The method comprises at least one intra-operative image acquisition phase 12, at least one an interventional image guidance phase 14, and at least one quality assurance check phase 16, following the interventional image guidance phase.

The image acquisition phase comprises receiving 18 computed tomography (CT) image data of an anatomical area which includes at least a portion of a kidney of a subject. This could be cone-beam CT image data or another type of CT image data.

The interventional image guidance phase 14, comprises receiving 20 real-time tool tracking data indicative of a positioning of an interventional tool for use in the interventional procedure. The interventional image guidance phase 14 further comprises generating 22 real-time guidance imagery based on the CT image data, and further based on the tracking data, the guidance imagery visualizing a position of the interventional tool relative to the anatomical area imaged in the CT image data. The interventional image guidance phase 14 further comprises communicating with a user interface device to display 24 the generated guidance imagery in real time on a display unit of the user-interface device.

The quality assurance check phase 16, following the interventional image guidance phase, comprises communicating with a CT imaging apparatus to acquire 26 further CT image data of said anatomical area using a CT imaging apparatus. This further CT image data is for use in visualizing any residual stones or stone fragments. This allows for determining whether complete stone removal has been achieved. In some examples, this could comprise, from the point of view of the computer implemented method, simply displaying the further CT image data to enable the clinician to determine whether complete stone removal has been achieved. Optionally, in some embodiments, the method comprises receiving a user input indicative of a clinician assessed check result: stone free or not stone free. In some embodiments, the stone free status could be automatically assessed by an image analysis algorithm. The quality assurance check phase preferably further comprises communicating with the user-interface device to display 28 the further CT image data on the display unit of the user interface.

In some embodiments, the further CT image data acquired in the quality assurance check phase is cone beam CT image data.

As noted above, the method can also be embodied in hardware form, for example in the form of a processing unit which is configured to carry out a method in accordance with any example or embodiment described in this document, or in accordance with any claim of this application.

Figure 2:
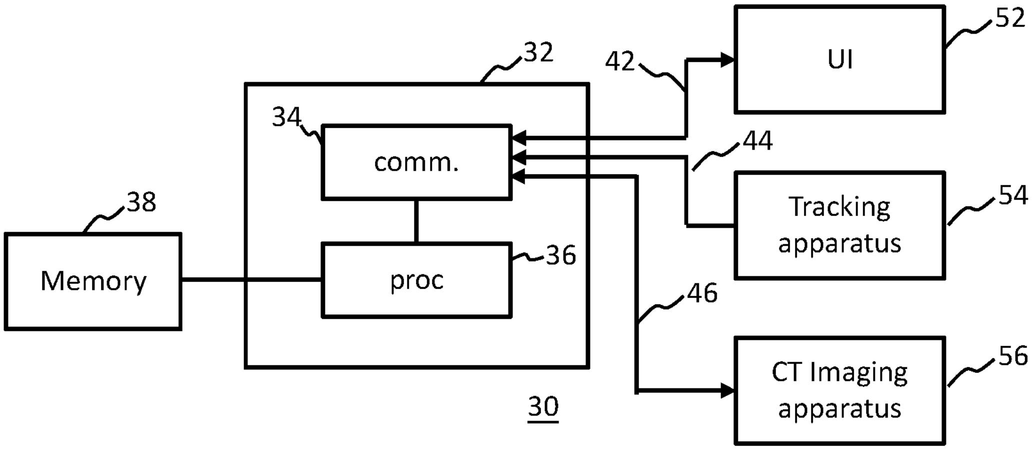
FIG. 2 outlines components of an example processing arrangement in accordance with one or more embodiments of the invention.

To further aid understanding, FIG. 2 presents a schematic representation of an example processing unit 32 configured to execute a method in accordance with one or more embodiments of the invention. The processing unit is shown in the context of a system 30 which comprises the processing unit. The processing unit alone represents an aspect of the invention. The system 30 is another aspect of the invention. The provided system does not have to comprise all of the illustrated hardware components; it may just comprise a subset of them.

The processing unit comprises one or more processors 36 configured to perform a method in accordance with that outlined above, or in accordance with any embodiment described in this document or any claim of this application. In the illustrated example, the processing unit further comprises a communication interface 34, or an input/output.

In the illustrated example of FIG. 2, the system 30 further comprises a user interface 52 which includes a display unit. The system further comprises an intra-operative CT imaging apparatus 56 (e.g. a cone-beam CT imaging apparatus). The system further comprises a tracking system or apparatus 56 for tracking a positioning of an interventional tool within the body of a patient. Of course, it is not essential that the system comprise all of these hardware components. A system in accordance with the invention can be provided which comprises none or only one or more of these components.

The communication interface 34 is adapted for receiving the previously mentioned CT image data, for outwardly communicating the previously mentioned guidance imagery to the user interface, for receiving the previously mentioned further CT image data, and for outwardly communicating the further CT image data to the user interface. The CT image data in the intra-operative imaging phase may be received from a CT imaging apparatus. It might alternatively be received from a datastore, or from an intermediary communication device, such as a hub server or a network node.

For example, the communication interface 34 may be adapted for wired or wireless connection to one or more external units. These might include any one or more of: the CT imaging apparatus 56 (e.g. cone beam CT imaging apparatus), the user interface device 52, and the tool tracking system or apparatus 54.

The system 30 may further comprise a memory 38 for storing computer program code (i.e. computer-executable code) which is configured for causing the one or more processors 36 of the processing unit 32 to perform the method as outlined above, or in accordance with any embodiment described in this disclosure, or in accordance with any claim.

As will be explained in more detail later, the system may further comprise one or more supplementary image data acquisition units. These might include for example one or more of: an ultrasound imaging system, and an endoscopic imaging system. The communication module may be adapted to communicate also with one or more of these supplementary image data acquisition units.

As mentioned previously, the invention can also be embodied in software form. Thus, another aspect of the invention is a computer program product comprising code means configured, when run on a processor, to cause the processor to perform a method in accordance with any example or embodiment of the invention described in this document, or in accordance with any claim of this patent application.

With regards to the processing unit 32, there are different options as to the implementation of this. In some embodiments, the processing unit may be a processing unit of the CT imaging apparatus. In some embodiments this may be the same processing unit which controls the image acquisition functions of the CT imaging apparatus. In some embodiments, it may be a dedicated processing unit comprised by the CT imaging apparatus. In some embodiments, the processing unit may be a dedicated processing unit provided separately to the CT imaging apparatus, for example provided in a dedicated housing. For example, in some embodiments, the processing unit may be comprised as part of an ambulatory unit, i.e. a mobile cart structure. By way of further example, in some embodiments, the processing unit might be a cloud-based processing unit.

References have been made above to intra-operative imaging. Intra-operative in the context of this disclosure means image acquisition performed contemporaneously with the intervention procedure. This is also sometimes known as per-operative imaging. In other words, this is imaging performed while the patient is in the operating room, or otherwise while the operation is ongoing. For example, it is performed on the same day as the interventional procedure for example.

The scope of the method does not necessarily need to include the process of actually acquiring the intraoperative image data. For example, the image data might have been acquired before the claimed method began, or in parallel with the claimed method, and wherein the claimed method comprises simply receiving already acquired image data. Of course, alternatively, the claimed method can include the step of acquiring the image data.

It is envisaged that the intra-operative image data could be image data acquired in the operating room itself, or a nearby imaging suite of the same institution.

It is envisaged that a mobile or moveable CT imaging apparatus could be used to acquire the image data, in particular an apparatus that is operable to be moved in and out of position to image the patient while the patient remains static on an operating table. A moveable system also allows the CT apparatus to be moved between different operating rooms. An alternative however is to provide a fixed CT imaging system, for instance mounted to the floor or ceiling of the operating room.

Reference has been made above to a preference for (particularly the intra-operative) CT image data to be cone beam image data. At least one reason for this preference is that cone-beam CT image data is capable of acquiring image data with a given resolution, and across a given volume, with a radiation dose to the patient which is lower than equivalent non-cone-beam systems. Another advantage is that cone-beam images can be acquired at greater speed than more traditional CT imagery techniques, due to the wider spatial spread of the x-ray beam. Thus, these advances in cone-beam CT imaging have made intra-operative CT imaging more practical and safer than has previously been the case, opening the possibility for using it to perform for instance the stone-free check of the present invention while renal access still remains open.

Reference is made above to an interventional tool. The interventional tool may for example include a percutaneous nephrolithotomy (PCN) needle. The interventional tool could include a dilator for passing over an inserted guidewire (inserted after insertion of the needle). The interventional tool could include a sheath. The interventional tool could include a nephroscope. In some cases, the interventional tool could include an ultrasound probe (e.g. for breaking down large stones). The interventional tool may comprise an obturator that is used for placing a cannula. In some examples, the cannula itself could be tracked.

In some examples, patient trackers may be placed on the patient, for use for example in registering tracking with CBCT imaging.

With regards to the tool tracking data and tool tracking system, a variety of options exist. Surgical tracking systems are known in the art. One example includes electromagnetic tracking. Another example includes optical tracking.

For example, a tracking system may be utilized which analyses oscillation of electromagnetic (EM) coils. In particular, one option is to incorporate at least one EM sensing element on or in the interventional tool comprising a coil, and wherein a reference electromagnetic field is generated by a transmitting coil arrangement positioned close to the patient. The reference field induces a current in the coil of the interventional tool, with electrical characteristics (particularly voltage amplitude) that depend upon the distance of the tool from the transmitting coil arrangement. This may necessitate a data connection to the sensor element in the tool from the tracking apparatus. In other examples, to avoid this, the tool can include the transmitting coil, and wherein a receive coil, or array of receive coils, are arranged close to the patient adapted to detect the electromagnetic signal emitted from the tool. Based on signal strength, a distance of the tool transmitter to the relevant receiver coil can be determined. More than one receiver or transmittal coil can be included on the tool, to allow for triangulation of tool position and/or orientation of the tool to be determined. Using these general concepts, it is possible to track the position of a tool in real-time.

In further examples, the tracking system may be configured to track the position of an object based on optical visual information. For example, a camera can be used to track the position of the tool based on visual tracking markers applied to the tool at one or a plurality of locations.

In all cases, the output of the tool tracking system 54 may be a data signal indicative of a coordinate position of the tool relative to a coordinate system of the tool tracking system.

For generating the guidance imagery, this may for example typically include a visual overlay indicative of a position of the interventional tool applied to or fused with an anatomical image representative of the anatomical area, the anatomical image being based on the CT image data acquired in the intra-operative image acquisition phase. In other words, this may typically be synthetic imagery, representing the real-time position of the tool relative to the earlier-acquired image. To this effect, the method may include a step of registering the relevant anatomical image spatially with the co-ordinate system of the tool tracking system. This can be done partially with input from a user in some examples. For example, a user might, as part of a calibration operation, touch the tool at a number of fiducial points on the body of the patient, to thereby calibrate the co-ordinate positions output from the tracking system for those points with the corresponding co-ordinate positions on the patient anatomy, as depicted in the images. For example, the points may be standard anatomical locations that are easily identifiable in the relevant anatomical image, and which the user could point to using a user input device or which could be detected automatically using image segmentation for example.

Optionally, in some embodiments, the interventional image guidance phase may further comprise receiving image data from one or more supplementary image data sources. For example, these may be real time imaging sources, so that live imagery can be used in addition to the synthetic imagery mentioned above. By way of example, these might include one or more of: real time endoscopic imaging data from an endoscopic imaging system; real-time ultrasound imaging data from an ultrasound imaging system; real-time fluoroscopic imaging data. The fluoroscopic imaging data could be provided by a dedicated fluoroscopic imaging device, or the cone-beam CT imaging apparatus mentioned previously may be adapted both for CT imaging and for fluoroscopic imaging, and such dual-mode CT systems are known in the art. Typically these may have for instance a C-arm construction of the gantry, permitting them to be moved in and out of place around the static patient. In the case of a dedicated fluoroscopy imaging device, this may be a digital x-ray device.

With regards to the optional endoscopic imaging system, this typically may comprise: one or more endoscopes; an imaging module carried by the one or more endoscopes, a light source carried by the one or more endoscopes, and a video processor for receiving a video image output from the imaging module. Various endoscopes might be used in the context of renal interventional procedures. These might include for instance any one or more of: cystoscope, nephroscope, ureteroscope, and ureterorenoscope).

An endoscopic imaging system might be provided, in part or in whole, as a part of at least one embodiment of the invention. For example, where the processing unit is provided housed by an ambulatory base station, the endoscopic imaging system could be docked or housed in the same base station, for ease of transport. Alternatively, the processing unit 32 previously referred to may simply be adapted to couple with an external endoscopic imaging system.

If supplementary image data is available, the image guidance phase may comprise: communicating with the user interface to simultaneously display the guidance imagery and the supplementary image data. For example, the two might be displayed side-by-side on the display unit of the user interface.

With regards to the quality assurance check phase, as has been mentioned previously, the confirmation of the stone free status (i.e. the result of the quality assurance check) can comprise one or both of an image review by the clinician performing the procedure, or an automated check based on application of a stone removal check algorithm to the obtained further CT image data to automatically determine complete or incomplete stone removal. With regards to the stone removal check algorithm, this makes use of computer aided detection methods. This could be applied in addition to the clinician checking the stone-free status in some examples, to further prevent missing residual stone fragments. In practice, this could be implemented by generating an output from the processing unit for causing the display unit of the user interface to display the further CT image data (so that the clinician can review the image(s)), and in addition applying the stone removal check algorithm, and displaying the result to the clinician on the display unit of the user interface.

In some embodiments, the method may further comprise receiving a user input indicative of the clinician's assessment of the stone free status. A negative result may trigger a further iteration of the image guidance phase.

With regards to the user interface, this may comprise a display unit for displaying the guidance imagery and any other information for presentation to the clinician. The user interface may further comprise at least one user input device. This may include for example one or more foot pedal controls. The user interface may include a touchscreen display, permitting user input by touch. The user interface, as a more general concept, may comprise one or more sterile control elements for use by the clinician within a sterile environment of the operating room, for providing user input to the user interface device. The system may additionally include a remote-control device for remotely controlling certain components of the system, such as the table height or the imaging equipment.

According to a preferred set of one or more embodiments, the system 30 comprises an ambulatory base station which houses or carries the processing unit 32 according to any of the embodiments described in this document, and which is for example moveable within or between operating rooms. A preferred solution for example comprises a single mobile cart that interoperates with all other hardware components of the system, including any optional hardware components mentioned in this disclosure previously or hereafter.

Using the system and method outlined above, the clinical procedure can be fully performed by a single clinician, e.g. a urologist (after anesthetizing the patient). For example, in practice, the patient may be placed in lithotomy position to insert a ureteral catheter, for example with the help of cystoscope under fluoroscopic guidance.

The patient may then be placed in prone position, such that the urologist can gain renal access using cone beam CT (CBCT) image data augmented with graphics to facilitate needle navigation. Fluoroscopic ultrasound, or other real time imaging modalities may additionally be used to assist. For CBCT and fluoroscopic imaging, a contrast agent may be administered through the ureteral catheter. Once renal access is confirmed by urine flow through the needle, the urologist will place and use a guidewire to dilate the access up to a 2 cm diameter, and subsequently perform the lithotripsy. Larger stone fragments may be collected through the access sheath, while smaller ones flush out automatically.

After stone removal, further CBCT images are acquired to confirm that all stone fragments are removed.

Finally, a renal drainage is made by placing either a JJ catheter or nephrostomy tube under fluoroscopy guidance, and the access sheath can be removed, closing the incision with a suture.

An example implementation of the method according to a particular set of embodiments will now be described by way of illustration of the above-summarized concepts. It will be appreciated that not all features of this particular set of embodiments are essential to the inventive concept, and are described to aid understanding and to provide an example to illustrate the inventive concepts.

Figure 3:
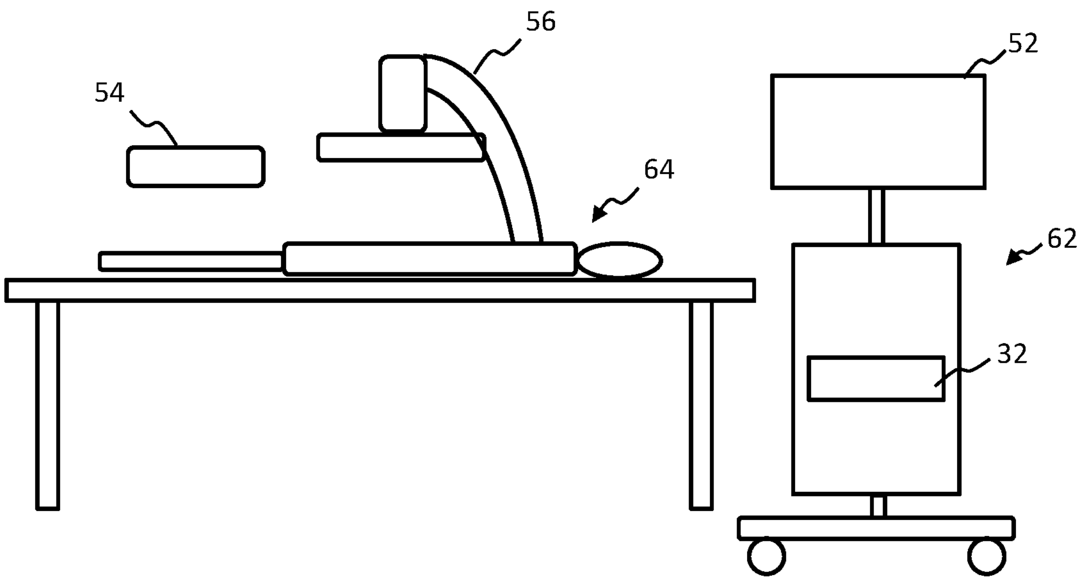
FIG. 3 schematically illustrates at least a subset of components of an example system, in operation, in accordance with one or more embodiments.

FIG. 3 schematically depicts a patient 64 during an example invention. Schematically illustrated is a cone beam CT imaging apparatus 56 having a C-arm construction. Further schematically illustrated is an example receiver coil unit 54 of an interventional tool tracking system. Further schematically illustrated is an example ambulatory base station 62 which houses a processing unit 32 adapted to perform the method in accordance with any of the examples or embodiments described in this disclosure. This might otherwise be referred to as a mobile cart. The base station 62 is mounted in this example on castors to permit it to be wheeled from place to place. Also mounted to the base station is a user interface 52 which includes a display unit. Alternatively, the user interface and/or display unit may be mounted elsewhere. The base station might also carry other optional hardware, such as a processor or control unit for any other supplementary imaging system used for the intervention, as already mentioned above.

The method includes an intraoperative image acquisition phase. This comprises acquiring CT image data of the internal anatomy of the kidney (urinary collecting system) and preferably also the portion of the subject's anatomy extending from the kidney to the body surface of the patient at which incision will be made for body access. The CT image data is preferably cone beam CT image data. It is preferred that the acquired CT image data is contrast-enhanced CT image data, however this is not essential.

In some embodiments the CT image data acquired in the at least one intra-operative image acquisition phase is itself contrast-enhanced cone beam CT image data.

Additionally, or alternatively, synthetic image data may be generated by fusing the CT image data received during the at least one intra-operative image acquisition phase with pre-operative image data of the same anatomical area of the same patient retrieved from a datastore. This may require registration of the pre-operative image(s) and the intra-operative image(s). The registration between intra-operative non-contrast CBCT images and pre-operative images may be performed using an image registration algorithm. Such algorithms are known in the art. In general, registration can be based on: image appearance, one or more fiducial markers (which may be trackable), segmentations of the kidney outline in both images; and/or segmentations of the renal parenchyma in both images. Segmentations can be performed using a segmentation algorithm, numerous examples of which are known in the art.

After intra-operative imagery has been acquired, the method may include an intervention planning phase before the intervention begins.

By way of example, the intervention planning phase may comprise steps of: obtaining an indication of a planned entry point to the kidney; and obtaining an indication of a planned entry path through the body to the entry point of the kidney. When image guidance imagery is then later generated for guiding the intervention, this can include imagery for guiding the clinician along the entry path to the entry point, in addition to the imagery showing the real-time location of the tool. For example, the guidance imagery may include one or more visual overlays providing navigation guidance for navigating insertion of the interventional tool along a pre-defined tool entry path from an incision point on the skin to the pre-defined entry point of the kidney. For example, the one or more visual overlays may provide navigation guidance provide a visual indication of a target location of the incision point and an indication of a target angle of insertion for the tool.

The indication of the planned entry point of the kidney may comprise an indication of a planned Calyx of the kidney through which kidney entry is to be achieved. Once the calyx of choice is known, the desired needle trajectory may be defined, either manually or automatically. The calyx of choice could be identified based on a manual or automatic segmentation or based on a location indicated by a user.

For instance, in some examples, the indication of the planned calyx of the kidney through which kidney entry is to be achieved is obtained based on a user input received at the user interface 52. In some examples, the planned entry path through the body and optionally a planned incision point are determined automatically based thereon. For example, the method might comprise obtaining an indication of a planned calyx for entry to the kidney, manually or automatically segmenting the said planned calyx within the received CT image data and identifying a location of a planned entry point of the kidney relative to the CT image data based thereon.

Therein follows an image guided intervention phase.

Here, given the desired needle trajectory, the clinician user can be supported to insert a tracked tool (e.g. a needle). Initially, the tracking may, as discussed above, assist the user to find a planned skin entry point, and/or to adopt a planned insertion angle of the tool in order to follow a planned entry path through the tissue, given a planned insertion point. While inserting the tracked tool under image guidance, the feedback provided by the visualization of the system will aid in obtaining renal access.

More specifically, it is proposed that guidance imagery is generated and rendered on the display unit of the user interface. This may advantageously comprise a visual overlay indicative of a position of the interventional tool fused with an anatomical image representative of the anatomical area. More particularly, the guidance imagery for example includes one or more visual overlays providing navigation guidance for navigating insertion of the interventional tool along a pre-defined tool entry path from an incision point on the skin to a pre-defined entry point of the kidney. For example, the one or more visual overlays providing navigation guidance may provide a visual indication of a target location of the incision point and an indication of a target angle of insertion for the tool.

It has already been explained above how the tool entry path can be planned in advance, either with input from the user or fully automatically. The resulting planned tool entry path may be stored for example as a trajectory defined by a series of co-ordinates along the path extension relative to a coordinate system of the tool tracking system or of the image data.

The anatomical image onto which the visual overlay is rendered can be based on the CT image data acquired in the intra-operative image acquisition phase. The anatomical image could simply be a CT image, or could be a synthetic fused image formed from the CT image and a pre-operative image.

Of course, a CT image dataset is 3D (volumetric) image data. Thus generating the guidance imagery may comprise extracting a relevant one or more 2D image planes from the 3D image data. If the CT image data is composed of a stack of axial 2D image slices, then one of these axial slices could be selected. Alternatively, multiplanar reformat (MPR) visualizations of the CBCT volume can be generated, using MPR techniques common in the art. In this way, a 2D slice through the 3D image field across any orientation can be generated. A user may be presented with user control options via the user interface to select a desired imaging plane orientation, or the most appropriate image plane view might be determined automatically, for example based on the tool tracking data, or based on a planned entry path through the body to the entry point of the kidney. For example, the image plane orientation may be selected which best visualizes the planned entry path. For example, the image plane orientation may be selected which is parallel with the planned insertion path, i.e. which contains the planned insertion path. In some examples, the optimum plane to visualize might be repeatedly updated as the tool moves, so that the plane view which is presented at each given update point is the plane which is parallel with at least the local section of the tool insertion path that the tool is currently positioned at (as determined by the tool tracking data). In other examples, the planar view upon which the graphical overlay of the tool position is rendered may be selected from a list of standard planar views, for example, one or more of the common orthogonal views: axial, sagittal, and coronal.

Of course, a further option is to generate guidance imagery which presents the tool position relative to multiple different planar views of the relevant anatomy, and to display all of these simultaneously.

A yet further option is to generate a volume rendering from the 3D CT image data for use in the guidance imagery. A volume rendering is a 2D image plane which presents a synthesized perspective view of a certain 3D object represented with a 3D image dataset. It is generated most typically based on ray-casting techniques in which, as part of a rendering algorithm, synthetic 'rays' are cast from a notional observer viewpoint through an image plane and into the imaged volume. The skilled person will be aware of common techniques for volume rendering.

In addition to the tracked tool position, optionally the presented guidance imagery may include one or more graphical indicia indicating segmentation boundaries of one or more anatomical features. This may further assist the clinician in navigating the anatomy. For example, one or more segmentation algorithms might be applied to the CT image data acquired in the intra-operative image acquisition phase to obtain segmentation data in advance of then generating the guidance imagery.

As mentioned previously, in addition to visualizing the tracked tool position relative to the CT image data, the method, in the interventional image guidance phase, may include displaying real time imagery of the anatomy, for example obtained from an ultrasound imaging system, a fluoroscopy imaging system and/or an endoscopic imaging system. For example, the image guidance phase may further comprise receiving supplementary image data comprising one or more of: real time endoscopic imaging data from an endoscopic imaging system; real-time ultrasound imaging data from an ultrasound imaging system; real-time fluoroscopic imaging data from a cone-beam CT imaging apparatus.

This could be presented simultaneously on the same display unit as is used to present the guidance imagery generated from the CT image data. Since the CT-based guidance imagery is partially synthetic (based on non-live CT imagery, fused with live tracking data), it may be helpful to a clinician to simultaneously see a live image of the anatomy to compare or corroborate what the guidance imagery formed from the CT data is showing.

By way of example, ultrasound imagery, when the patient is in the prone position, would typically obtain an oblique view, with the tool (e.g. needle) in-plane. By way of example, fluoroscopy, when the patient is in the prone position and the x-ray generator is above the patient, would typically generate a view plane perpendicular to the needle (i.e. the so-called “bull’s eye view”).

The guidance imagery, using the live tool tracking data, assists the user in: (a) navigating to the planned entry point of the kidney (i.e. renal entry); and (b) in performing the stone removal procedure one renal entry has been achieved.

It has been described above, that an intra-operative image acquisition phase can be performed in advance of the intervention beginning in order to obtain (preferably cone-beam) CT image data of the patient for use in generating the guidance imagery.

Additionally or alternatively, in some embodiments, one or more intra-operative image acquisition phases may be performed after the interventional procedure has begun, during the interventional procedure. This may be to update the CT image data for example. This can make use for example of a cone-beam CT imaging apparatus. This can make use of an imaging apparatus which is moveable into and out of place for imaging the patient without moving the patient, e.g. a C-arm structure. Such imaging performed during the intervention may be performed during an induced apnea of the patient, meaning temporary cessation of breathing. This avoids the negative impact of breathing motion. During the interventional procedure, the patient is typically anesthetized. To this end, the patient is intubated and connected to a ventilator that is continuously operated and monitored by the anaesthesiologist. In this situation, the patient’s breathing is under control, making it easy to cease the breathing for e.g. 45 seconds during which a scan is made.

Once stone removal has been performed, the proposed computer implemented method involves a quality assurance check phase.

The bright appearance of kidney stones makes per-operative (intra-operative) CBCT imaging particularly suitable for confirming the stone free status of the patient at the end of a PCNL procedure.

The quality assurance check phase might be triggered in practice responsive to receipt of a pre-defined user input command from the user interface. In other words, the clinician indicates that stone removal has been completed and that the quality check should begin.

To confirm the stone free status, further CT image data is acquired representative of the kidney. This is preferably a non-contrast enhanced cone beam CT scan. Such a scan is performed intra-operatively, while renal access remains open. The resulting CT image data may be rendered and presented to the clinician on the user interface display. Confirmation of the stone free status may be achieved by simple image review by the clinician. The clinician may input an indication of a result of the image review, and thus a result of the quality assurance check, via the user interface, which may be recorded and/or may trigger one or more subsequent actions.

Additionally or alternatively, computer aided detection methods may be applied to the acquired further CT image data to detect presence of any residual stone fragments. Thus in this case, an indication of the result of the quality assurance check may be obtained based on application of a stone removal check algorithm to the obtained further CT image data to automatically determine complete or incomplete stone removal.

In CT and CBCT imaging, stones appear as bright regions in the image due to their composition. In other words, kidney stones have a different Hounsfield density value than surrounding tissues.

An example stone removal check algorithm may be configured to identify such bright objects within the kidney.

The steps of an example algorithm could include the following:

(1) Segment the kidney within the CT image (e.g. using an AI segmentation model or traditional methods such as Active Contours, Active Appearance Models, or Active Shape Models).

(2) Locate bright objects within the kidney (i.e. exceeding a certain Hounsfield density value).

(3) Optionally, filter the detected objects based on a size range, to prevent false positives, as well as to avoid detection of small fragments that do not require any attention from the doctor.

The further CT image data used for the quality assurance check may be visualized using for example multi-planar reformatting to obtain one or more planar views representing the internal anatomy of the kidney. For example, a set of two or more orthogonal planar views of the anatomy may be presented. Another option is to apply volume rendering to generate one or more volume rendered views of the anatomy. Preferably, these might be generated so as to visualize a 3D perspective view of any residual stone fragments. Various techniques exist for volume rendering, for example direct volume rendering or maximum intensity projection, and the skilled person will be aware of the different options for applying this rendering approach.

Optionally, the further CT image data may be processed with further visual overlays to provide supplementary information. For example, overlays might include one or more segmentation overlays representative of the renal anatomy, for example including parenchyma, urinary collecting system, etc. In some examples, overlays might include a visual overlay representative of the live tool tracking position.

Preferably, the further CT image data acquired in the quality assurance check phase may be manipulable in terms of the rendered view presented via user controls of the user interface. For example, the user controls may permit panning, rotating, or scrolling. The user controls may be sterile user controls, e.g. foot pedals, or a sterilizable touch screen display, or a sterilizable keypad or joystick.

If the result of the quality assurance check is negative, i.e. residual stone pieces are still present, the surgical user can immediately intervene and remove residual stone fragments. This is aided by the known location of the residual stone fragments, as shown on the CT imagery. Indeed, in some advantageous embodiments, the quality assurance check phase may comprise: obtaining, based on user input or based on an automated segmentation algorithm, location information associated with any residual stones present in the kidney; and guidance imagery which includes a visualization of the location information associated with residual stones.

For example, the method may further comprise: obtaining an indication of a result of the quality assurance check; and responsive to the result of the quality assurance check indicating incomplete stone removal, controlling execution of a further iteration of the interventional image-guidance phase, and, optionally, subsequently a further execution of the quality assurance check phase. The result might be obtained automatically or from a user-input, as has already been discussed. Optionally, the further iteration of the interventional image guidance phase may include generating further guidance imagery comprising a visual overlay indicative of a position of the interventional tool fused with an anatomical image representative of the anatomical area. Preferably the anatomical image in this iteration may be based on the further CT image data acquired in the quality assurance check phase. In this case, it may not in fact be necessary to obtain location information of the residual stones and to overlay this on the CT image data, since the further CT image data would already include a visual representation of the stone fragments. Of course, to aid visualization, graphical overlays indicative of the stone fragment positions might additionally be added, e.g. indicating outlines, or highlights indicating area/volume coverage of stone fragments.

Once the further iteration of the image guidance phase is complete, optionally, another iteration of the quality assurance check might be performed to re-check the stone free status. Of course, this might also be omitted. Here, the clinician might be given the option, via the user interface, to either repeat the check or not. Here, a balance might need to be decided between further exposing the patient to radiation versus better guaranteeing complete stone removal.

In some embodiments, archiving of all of the acquired intraoperative image data might be facilitated by an operative coupling of the processing unit 32 with a DICOM interface permitting export of medical image data to one or more databases. These might be third party databases or local hospital databases. The export might for example be to a PACS or other DICOM node.

By way of brief summary of the above, an example workflow for the intervention might be as follows.

First, per-operative (intraoperative) CBCT imaging is performed. The user may subsequently define, via the user interface, the calyx of choice for gaining entry to the kidney, and indicate the desired needle entry path. This might be facilitated by dedicated clinical application software executed by the processing unit 32. Then, the user is supported by visual overlays of real-time tool tracking data on the CT image data to insert a tracked needle to obtain renal access. Improved visualization of the internal anatomy of the kidney (urinary collecting system) may optionally be achieved by using a contrast medium when acquiring the CT image data, or by fusing pre-operative contrast enhanced CT image data with the intra-operative CT image data before generating the visual overlay renderings. The registration between intra-operative CBCT images and pre-operative images may for example be based on any one or more of: image appearance; fiducial markers (trackable or non-trackable); segmentations of the kidney outline in both images; segmentations of the renal parenchyma in both images. Registration techniques are well known in the art. As already discussed, the calyx of choice can be identified by: a segmented region (manually/automatically) or a location indicated by the user. Subsequently, while inserting the tracked needle under image guidance, the feedback provided by the visualization (the guidance imagery) of the system will aid in obtaining renal access and in stone removal. Following this, further CT image data can be acquired as part of a quality assurance stone-free check.

As has been discussed, embodiments make use of a user interface display unit to display the guidance imagery and to display the further CT image data used for checking stone-free status.

In an advantageous set of embodiments, it is proposed to provide the processing unit with capability to receive video input from a plurality of different imaging modalities. This has already been discussed above, wherein it has been explained that real-time imaging feeds from ultrasound, fluoroscopic, endoscopic or any other imaging modalities may be received and presented on the display unit of the user interface. These one or more further video feeds may in some embodiments be presented continuously, independently of the different stages of the primary method discussed above in relation to FIG. 1. In other words, in some embodiments, it is proposed that the processing unit host two parallel operations: one of video rendering and presentation on the display on the user interface display unit of one or more live video feeds, and a second comprising the steps of the method as outlined for example in FIG. 1, in which guidance imagery is generated from CT image data and presented also on the display unit.

The video display functionality may therefore provide means for connection of a plurality of different video inputs, enabling e.g., side-by-side, display of endoscopic imaging, real-time fluoroscopic imaging or ultrasound imaging. This is convenient for example during the placement of the ureteral catheter at the start of the procedure, and during the placement of the J-J catheter or nephrostomy at the end of the procedure.

In addition, the processing unit 32 may include functionality for capturing image snapshots, or video clip recording, for storage and archive. The processing unit may include functionality permitting export of these, for example via a DICOM interface operatively coupled with the processing unit.

Advantageously, the optional video display can help support all stages of the renal interventional procedure.

Embodiments of the invention described above employ a processing unit. The processing unit may in general comprise a single processor or a plurality of processors. It may be located in a single containing device, structure or unit, or it may be distributed between a plurality of different devices, structures or units. Reference therefore to the processing unit being adapted or configured to perform a particular step or task may correspond to that step or task being performed by any one or more of a plurality of processing components, either alone or in combination. The skilled person will understand how such a distributed processing arrangement can be implemented. The processing unit may include a communication module or input/output for receiving data and outputting data to further components.

In some embodiments, the system acquires a non-contrast enhanced intra-operative CBCT image and enhancing the image with the help of segmentation techniques and/or computer-aided detection for detecting residual stones; acquiring an end-of-procedure stone-free check CBCT image including segmentation of residual stones; presenting the 2 images side-by-side, or fusing or otherwise combining the images to show the abundance and absence of residual stones.

In some embodiments, the CBCT image may further include overlays of renal anatomy and current device locations.

In some embodiments, an anatomical structure of the patient is being generated. The system generates guidance support (e.g. through a guidance line), wherein the guidance line can be automatically drawn from the inner tip of access point to the residual stone.

In some embodiments, the system may provide feedback to the user on the absence/abundance of residual stones.

The one or more processors of the processing unit can be implemented in numerous ways, with software and/or hardware, to perform the various functions required. A processor typically employs one or more microprocessors that may be programmed using software (e.g., microcode) to perform the required functions. The processor may be implemented as a combination of dedicated hardware to perform some functions and one or more programmed microprocessors and associated circuitry to perform other functions.

Examples of circuitry that may be employed in various embodiments of the present disclosure include, but are not limited to, conventional microprocessors, application specific integrated circuits (ASICs), and field-programmable gate arrays (FPGAs).

In various implementations, the processor may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

A single processor or other unit may fulfill the functions of several items recited in the claims.

The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

If the term "adapted to" is used in the claims or description, it is noted the term "adapted to" is intended to be equivalent to the term "configured to".

Any reference signs in the claims should not be construed as limiting the scope.

The invention claimed is:

1. A processing unit for providing interventional support during a renal interventional procedure for kidney stone removal, the processing unit comprising one or more processors configured to:

perform at least one intra-operative image acquisition phase, comprising:

receiving computed tomography (CT) image data of an anatomical area which includes at least a portion of a kidney of a subject;

perform an interventional image guidance phase, comprising:

receiving real-time tool tracking data indicative of a position of an interventional tool for use in the renal interventional procedure, generating real-time guidance imagery based on the CT image data and the real-time tool tracking data to guide renal access along an access path, wherein the guidance imagery visualizes the position of the interventional tool relative to the anatomical area imaged in the CT image data, communicating with a user interface device to display the guidance imagery in real time on a display unit of the user interface device;

perform a quality assurance check phase intra-operatively while the renal access remains open, following the interventional image guidance phase, comprising:

communicating with a CT imaging apparatus to acquire further CT image data of the anatomical area using the CT imaging apparatus, for use thereby in determining whether complete stone removal has been achieved, wherein the further CT image data is cone beam CT image data, applying an automated stone-removal check algorithm to the further CT image data for detecting residual stones or stone fragments and determining location information associated with the detected residual stones or stone fragments; and communicating with the user interface device to display the further CT image data on the display unit of the user interface device; and responsive to the detecting of the residual stones or stone fragments, control execution of a further iteration of the interventional image guidance phase while the renal access remains open, wherein the guidance imagery in the further iteration is based on the further CT image data.

2. The processing unit of claim 1, wherein, during the further iteration of the interventional image guidance phase, the guidance imagery includes a visualization of the location information associated with residual stones.

3. The processing unit of claim 1, wherein the at least one intra-operative image acquisition phase comprises communicating with the CT imaging apparatus to acquire the cone beam CT image data of the anatomical area using the CT imaging apparatus.

4. The processing unit of claim 1, wherein generating the guidance imagery comprises:

generating synthetic image data by fusing the CT image data received during the at least one intra-operative image acquisition phase with pre-operative image data of the anatomical area of the subject retrieved from a datastore.

5. The processing unit of claim 1, wherein the interventional image guidance phase further comprises:

receiving supplementary image data comprising at least one:

real time endoscopic imaging data from an endoscopic imaging system, real-time ultrasound imaging data from an ultrasound imaging system, or real-time fluoroscopic imaging data from a cone-beam CT imaging apparatus; and communicating with the user interface device to simultaneously display the guidance imagery and the supplementary image data.

6. An ambulatory base station being moveable within an operating room, and comprising the processing unit of claim 1.

7. The processing unit of claim 1 further comprising:

a cone-beam CT imaging apparatus; and a tracking system for tracking the position of an interventional tool within a body of the subject.

8. The processing unit of claim 1, wherein the guidance imagery comprises a visual overlay indicative of the position of the interventional tool fused with an anatomical image representative of the anatomical area, the anatomical image being based on the CT image data acquired in the at least one intra-operative image acquisition phase.

9. The processing unit of claim 8, wherein the guidance imagery further includes one or more visual overlays providing navigation guidance for navigating insertion of the interventional tool along a pre-defined tool entry path from an incision point on a skin to a pre-defined entry point of the kidney.

10. The processing unit of claim 9, wherein the one or more visual overlays providing navigation guidance are configured to provide a visual indication of a target location of the incision point and an indication of a target angle of insertion for the interventional tool.

11. The processing unit of claim 9, wherein the one or more processors are further configured to perform an intervention planning phase comprising:

obtaining an indication of a planned entry point of the kidney; and obtaining an indication of the pre-defined tool entry path through a body of the subject to the planned entry point of the kidney, wherein the one or more visual overlays for providing navigation guidance are generated based on the obtained indications of the planned entry point and the pre-defined tool entry path.

12. The processing unit of claim 11, wherein the indication of the planned entry point of the kidney comprises an indication of a planned Calyx of the kidney through which kidney entry is to be achieved.

13. The processing unit of claim 1, further comprising a communication interface for wired or wireless connection to one or more of:

a cone-beam CT imaging apparatus, the user interface device, and a tool tracking system.

14. The processing unit of claim 13, further comprises another communication interface for wired or wireless connection to at least one of an ultrasound imaging system and an endoscopic imaging system.

15. The processing unit of claim 1, wherein the stone-removal check algorithm comprises:

segmenting the kidney within the further CT image; and locating bright objects within the kidney based on the segmenting.

16. The processing unit of claim 15, wherein the stone-removal check algorithm further comprises:

filtering the bright objects based on a size range to prevent false positives and to avoid detection of small fragments that do not require further attention.

17. A computer-implemented method for interventional support during a renal interventional procedure for kidney stone removal, the method comprising:

performing at least one intra-operative image acquisition phase, comprising:

receiving computed tomography (CT) image data of an anatomical area which includes at least a portion of a kidney of a subject;

performing an interventional image guidance phase, comprising:

receiving real-time tool tracking data indicative of a position of an interventional tool for use in the renal interventional procedure;

generating real-time guidance imagery based on the CT image data and the real-time tool tracking data to guide renal access along an access path, the guidance imagery visualizing the position of the interventional tool relative to the anatomical area imaged in the CT image data;

communicating with a user interface device to display the guidance imagery in real time on a display unit of the user interface device; and performing a quality assurance check phase intra-operatively while the renal access remains open, following the interventional image guidance phase, comprising:

communicating with a CT imaging apparatus to acquire further CT image data of the anatomical area using the CT imaging apparatus, for use thereby in determining whether complete stone removal has been achieved, wherein the further CT image data is cone beam CT image data;

applying an automated stone-removal check algorithm to the further CT image data for detecting residual stones or stone fragments and determining location information associated with the detected residual stones or stone fragments; and communicating with the user interface device to display the further CT image data on the display unit of the user interface device; and responsive to the detecting of the residual stones or stone fragments, controlling execution of a further iteration of the interventional image guidance phase while the renal access remains open, wherein the guidance imagery in the further iteration is based on the further CT image data.

18. The method of claim 17, wherein the stone-removal check algorithm comprises:

segmenting the kidney within the further CT image; and locating bright objects within the kidney based on the segmenting.

19. A non-transitory computer readable medium storing instructions for interventional support during a renal interventional procedure for kidney stone removal that, when executed by one or more processors, cause the one or more processors to:

perform at least one intra-operative image acquisition phase, comprising:

receiving computed tomography (CT) image data of an anatomical area which includes at least a portion of a kidney of a subject;

perform an interventional image guidance phase, comprising:

receiving real-time tool tracking data indicative of a position of an interventional tool for use in the renal interventional procedure;

generating real-time guidance imagery based on the CT image data and the real-time tool tracking data to guide renal access along an access path, the guidance imagery visualizing the position of the interventional tool relative to the anatomical area imaged in the CT image data;

communicating with a user interface device to display the guidance imagery in real time on a display unit of the user interface device; and perform a quality assurance check phase intra-operatively while the renal access remains open, following the interventional image guidance phase, comprising:

communicating with a CT imaging apparatus to acquire further CT image data of the anatomical area using a CT imaging apparatus, for use thereby in determining whether complete stone removal has been achieved, wherein the further CT image data is cone beam CT image data;

applying an automated stone-removal check algorithm to the further CT image data for detecting residual stones or stone fragments and determining location information associated with the detected residual stones or stone fragments; and communicating with the user interface device to display the further CT image data on the display unit of the user interface device; and responsive to the detecting of the residual stones or stone fragments, control execution of a further iteration of the interventional image guidance phase while the renal access remains open, wherein the guidance imagery in the further iteration is based on the further CT image data.

20. The non-transitory computer readable medium of claim 19, wherein the stone-removal check algorithm comprises:

segmenting the kidney within the further CT image; and locating bright objects within the kidney based on the segmenting.

* * * * *